US010073039B2

(12) United States Patent
Natrajan et al.

(10) Patent No.: US 10,073,039 B2
(45) Date of Patent: Sep. 11, 2018

(54) DEGRADABLE CATIONIC SURFACTANTS AND USE THEREOF IN ENHANCING CHEMILUMINESCENCE

(71) Applicant: SIEMENS HEALTHCARE DIAGNOSTICS INC., Tarrytown, NY (US)

(72) Inventors: Anand Natrajan, Manchester, NH (US); David Wen, Northborough, MA (US)

(73) Assignee: SIEMENS HEALTHCARE DIAGNOSTICS, INC., Tarrytown, NY (US)

(*) Notice: Subject to any disclaimer, the term of this patent is extended or adjusted under 35 U.S.C. 154(b) by 0 days.

(21) Appl. No.: 14/891,262

(22) PCT Filed: May 13, 2014

(86) PCT No.: PCT/US2014/037914
§ 371 (c)(1),
(2) Date: Nov. 13, 2015

(87) PCT Pub. No.: WO2014/186406
PCT Pub. Date: Nov. 20, 2014

(65) Prior Publication Data
US 2016/0131588 A1 May 12, 2016

Related U.S. Application Data

(60) Provisional application No. 61/823,162, filed on May 14, 2013.

(51) Int. Cl.
G01N 21/76 (2006.01)
G01N 33/58 (2006.01)
C12Q 1/66 (2006.01)

(52) U.S. Cl.
CPC ............ *G01N 21/76* (2013.01); *C12Q 1/66* (2013.01); *G01N 33/582* (2013.01)

(58) Field of Classification Search
CPC ......... C12Q 1/66; G01N 33/582; G01N 21/76
See application file for complete search history.

(56) References Cited

U.S. PATENT DOCUMENTS 4,228,042 A 10/1980 Letton
4,927,769 A 5/1990 Chang et al.
(Continued)

FOREIGN PATENT DOCUMENTS

CN 101226200 7/2008
CN 102311731 1/2012
(Continued)

OTHER PUBLICATIONS

Anand Natrajan et al: Facile N-alkylation of acridine esters with 1,3-propane sultone in ionic liquids, The Royal Society of Chemistry 2011, Green Chemistry, vol. 13, No. 4, Jan. 1, 2011, pp. 913-921.
(Continued)

Primary Examiner — Shafiqul Haq
(74) Attorney, Agent, or Firm — Kevin Stein

(57) ABSTRACT

The present invention relates to methods of enhancing chemiluminescence from a chemiluminescent label comprising contacting a chemiluminescent label with an acid in the presence of a degradable cationic surfactant and hydrogen peroxide followed by the addition of a base. Related kits containing such degradable cationic surfactant are also provided. The degradable cationic surfactant can compress light emission time of the chemiluminescent label to an extent that is comparable to or shorter than conventional surfactants. The degradable cationic surfactant can also increase chemiluminescence of the chemiluminescent label, provid- (Continued)

ing increased light emission output that is comparable to conventional surfactants.

20 Claims, 7 Drawing Sheets

(56) References Cited

U.S. PATENT DOCUMENTS

| | | | |
|---|---|---|---|
| 5,656,426 | A | 8/1997 | Law et al. |
| 6,664,043 | B2 | 12/2003 | Natrajan et al. |
| 7,781,588 | B1 | 8/2010 | Wang et al. |
| 7,875,467 | B2 | 1/2011 | Natrajan et al. |
| 8,034,636 | B2 | 10/2011 | Evangelista et al. |
| 8,119,422 | B2 | 2/2012 | Natrajan et al. |
| 2006/0166840 | A1 | 7/2006 | Miller |
| 2008/0248493 | A1 | 10/2008 | Mattingly et al. |
| 2010/0256380 | A1 | 10/2010 | Natrajan et al. |
| 2013/0168620 | A1* | 7/2013 | Guo .................... F21K 2/06 252/700 |

FOREIGN PATENT DOCUMENTS

| | | |
|---|---|---|
| CN | 105264377 B | 1/2016 |
| JP | H07278184 | 10/1995 |
| JP | H08313443 | 11/1996 |
| JP | H1081900 | 3/1998 |
| JP | 2001097840 | 4/2001 |
| JP | 2002128744 | 5/2002 |
| JP | 2005503431 | 2/2005 |
| JP | 2013510934 | 3/2013 |
| WO | 96/02839 | 2/1996 |
| WO | 2011060228 | 5/2011 |
| WO | 2014/011762 | 1/2014 |

OTHER PUBLICATIONS

Anand Natrajan et al, "Chemiluminescence from alkoxy-substituted acridinium dimethylphenyl ester labels", The Royal Society of Chemistry 2012, Organic & Biomolecular Chemistry, GB, Jan. 1, 2012, vol. 10, No. 17, p. 3432-3447.
Anand Natrajan et al, "Effect of surfactants on the chemiluminescence of acridinium dimethylphenyl ester labels and their conjugates", The Royal Society of Chemistry 2011, Organic & Biomolecular Chemistry, GB, Jan. 1, 2011, vol. 9, No. 14, pp. 5092-5103.
Anand Natrajan et al, "Chemiluminescence from alkoxy-substituted acridinium dimethylphenyl ester labels", The Royal Society of Chemistry 2012, Electronic Supplementary Material for Organic & Biomolecular Chemistry, pp. 1-35, Retrieved from the Internet: URL:http//www.rsc.org/suppdata/ob/c2/c2ob00022a/c2ob00022a. pdf, retrieved on Oct. 27, 2016.
Taisuke Banno et al, "Synthesis and properties of biodegradable and chemically recyclable cationic surfactants containing carbonate linkages", Journal of Oleo Science, (Aug. 11, 2007), vol. 56, No. 9, pp. 493-499, XP055314657 [Y] 1-17 *the whole document*.
Taisuke Banno et al, "Creation of Novel Green and Sustainable Gemini-Type Cationics Containing Carbonate Linkages", Journal of Surfactants and Detergents, Springer, Berlin, DE, (Oct. 10, 2010), vol. 13, No. 4, doi:10.1007/S11743-010-1224-5, ISSN 1097-3958, pp. 387-398, XP001557625 [Y] 1-17 *the whole document*.
Susana Shimizu et al, "2-(Acylaminoethyl)trimethylammonium chloride surfactants: synthesis and properties of aqueous solutions", Colloid & Polymer Science, DE, (Dec. 1, 2003), vol. 282, No. 1, doi:10.1007/s00396-003-0897-y, ISSN 0303-402X, pp. 21-31, XP055314661 [Y] 1-17 *the whole document*.
Anand Natrajan et al, "Use of degradable cationic surfactants with cleavable linkages for enhancing the chemiluminescence of acridinium ester labels", RSC Advances, (Nov. 28, 2013), vol. 3, No. 44, doi:10.1039/c3ra44461a, p. 21398, XP055314649 [PX] 1-17 *the whole document*.
PCT Search Report and Written Opinion dated Nov. 13, 2014 for International Application No. PCT/US2014/037914, 9 pp.
Dantoni Patricia et al. "Effect of some surfactants on the chemiluminescent reactions of bis(2,4,6-trichlorophenyl)oxalate and bis(2-nitrophenyl) oxalate with hydrogen peroxide" Published by NRC Research Press; Can. J. Chem. 90: pp. 534-541 (2012) / Jun. 30, 2012.
European Search Report dated Nov. 14, 2016 for Application No. 14798016.3-1408, pp. 1-10.
Anand Natrajan et al, "Supplementary Material, Effect of surfactants on the chemiluminescence of acridinium dimethylphenyl ester labels and their conjugates", Retrieved from the Internet: URL:http://www.rsc.org/suppdata/ob/cI/clob05543g/ clob05543g.pdf on Oct. 10, 2017, pp. 1-17.

* cited by examiner

A

B

A

Cationic surfactant with cleavable amide linkage, CMC = 0.64 mM

Cationic surfactant with cleavable carbonate linkage, CMC = 0.43 mM for iodide salt

B

DEGRADABLE CATIONIC SURFACTANTS AND USE THEREOF IN ENHANCING CHEMILUMINESCENCE

CROSS-REFERENCE TO RELATED APPLICATIONS

This application claims priority to U.S. Provisional Application Ser. No. 61/823,162 filed May 14, 2013, which is incorporated herein by reference in its entirety.

FIELD OF THE INVENTION

The present invention relates to environmentally friendly, degradable cationic surfactants for enhancing the chemiluminescence of acridinium compounds. Related methods and kits are also provided.

BACKGROUND OF THE INVENTION

Chemiluminescent acridinium dimethylphenyl esters are highly sensitive labels (FIG. 1B) that are used for the measurement of a wide range of clinically important analytes in automated immunoassays such as Siemens Healthcare Diagnostics' ADVIA: Centaur® systems. At the end of each assay, light emission from the acridinium ester label is triggered by the sequential addition of two reagents. An initial treatment with 0.3 mL of 0.1 M nitric acid (also containing 0.5% hydrogen peroxide) converts the non-chemiluminescent pseudobase of the acridinium ester (FIG. 1A) to the chemiluminescent acridinium form of the label. Subsequent addition of 0.3 mL of 0.25 M sodium hydroxide also containing 7 mM of the cationic surfactant cetyltrimethylammonium chloride (CTAC), ionizes the hydrogen peroxide and initiates light emission. The surfactant CTAC plays a very important role in the chemiluminescence process of acridinium esters (Natrajan et al, *Org. Biomol. Chem.*, 2011, 9, 5092-5103). CTAC compresses emission times of the labels from approximately 60 s to <5 seconds. CTAC also increases overall light output 3-4 fold from acridinium ester labels and their conjugates. Faster light emission and increased light output enable fast and sensitive assays in automated instruments such as in Siemens Healthcare Diagnostics' ADVIA: Centaur® systems.

Each immunoassay test performed on the ADVIA: Centaur® system consumes approximately 0.7 mg of CTAC. The very large volume of immunoassay tests that are performed worldwide on the ADVIA: Centaur® systems (>500 million tests in 2012 alone based on one estimate) results in the annual usage of substantial quantities (>350 kg) of this cationic surfactant. Cationic surfactants such as CTAC are considered to be quite toxic to aquatic life when they are discharged into the environment (Nałęcz-Jawecki et al, *Ecotoxicology and Environmental Safety*, 2003, 54, 87-91; Pantani et al, *Bull. Environ. Contamin. Toxicol.*, 1995, 55, 179-186; Kümmurer et al, *J. Chromatogr. A*, 1997, 774, 281-286; Sütterlin et al, *Ecotoxicology and Environmental Safety*, 2008, 71, 498-505; Roberts and Costello, *QSAR*, 2003, 22, 220-225; Leeuwen et al, *Chemosphere*, 1992, 24, 629-639). Although cationic surfactants are degraded by microbes under aerobic conditions, under anaerobic conditions they are persistent and show little biodegradation thereby posing a serious environmental risk to aquatic life (Ying, *Environment International*, 2006, 32, 417-431; Maden in *Biodegradability and Toxicity of Surfactants*, Handbook of Detergents Part B: Environmental Impact, U. Zoller, Editor, Marcel Dekker, 2004, p 211-248; Ying in *Distribution, Behavior, Fate and Effects of Surfactants and their Degradation Products in the Environment*, Handbook of Detergents Part B: Environmental Impact, U. Zoller, Editor, Marcel Dekker, 2004, p 77-109).

Thus, a long-felt need remains to replace CTAC with degradable and environment friendly ("green") surfactants, while preserving the efficiency of chemiluminescence enhancement. It is therefore an object of the present invention to provide green surfactants that are at least as efficient as CTAC in enhancing chemiluminescence.

SUMMARY OF THE INVENTION

In accordance with the foregoing objectives and others, it has surprisingly been found that the chemiluminescence of chemiluminescent acridinium compounds are enhanced by incorporating degradable surfactants into light triggering reagents, to a degree that is at least comparable to that of conventional surfactants such as CTAC. The use of these environmentally friendly surfactants in light triggering reagents for widely used acridinium labels is a green and in some embodiments, unexpectedly more effective alternative to the conventional cationic surfactant CTAC.

In one aspect, a method of enhancing chemiluminescence from a chemiluminescent label is provided comprising contacting a chemiluminescent label with an acid and hydrogen peroxide in the presence of a degradable cationic surfactant having formula I:

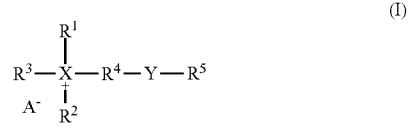

wherein:
X is nitrogen or phosphorus;
$R^1$, $R^2$ and $R^3$ are each independently selected from hydrogen and an alkyl, alkenyl, alkynyl, cycloalkyl or aralkyl group optionally having one or more heteroatoms;
$R^4$ and $R^5$ are each independently selected from an alkyl, alkenyl, alkynyl, cycloalkyl or aralkyl group optionally having one or more heteroatoms;
Y is a cleavable linkage; and
$A^-$ is an anionic counterion to $X^+$.

In some embodiments, the chemiluminescent label can be an acridinium dimethylphenyl ester, an acridinium sulfonamide, or a derivative or conjugate thereof. The acid can be nitric acid.

In certain embodiments, the method can further include compressing light emission time of said chemiluminescent label, thereby providing a compressed emission time than a standard emission time without surfactants, wherein said compressed emission time is comparable to that of cetyltrimethylammonium chloride. For example, the compressed emission time may be shorter (e.g., about 20%, about 30% or about 50% shorter) than that of cetyltrimethylammonium chloride. In one embodiment, the surfactant of the present invention is as effective as cetyltrimethylammonium chloride in enhancing total light yield of the chemiluminescent label.

In some embodiments, the method can further include increasing chemiluminescence of said chemiluminescent label, thereby providing an increased light emission than a standard light emission without surfactants, wherein said increased light emission is comparable to that of cetyltrimethylammonium chloride. For example, said increased light emission may be at least about 2.5 fold enhancement compared to the standard light emission without surfactants. In certain embodiments, said enhancement can be at least about 70%, at least about 80% or at least about 90% that of cetyltrimethylammonium chloride. In an embodiment, the surfactant of the present invention is at least as effective as cetyltrimethylammonium chloride in compressing emission time of the chemiluminescent label.

In various embodiments, $R^1$, $R^2$ and $R^3$ can be each independently a $C_{1-10}$ alkyl, $C_{2-10}$ alkenyl, $C_{2-10}$ alkynyl, $C_{3-10}$ cycloalkyl or $C_{4-10}$ aralkyl group optionally having one or more heteroatoms. $R^4$ can be a $C_{1-20}$ alkyl, $C_{2-20}$ alkenyl, $C_{2-20}$ alkynyl, $C_{3-20}$ cycloalkyl or $C_{4-20}$ aralkyl group optionally having one or more heteroatoms. $R^5$ can be a $C_{1-30}$ alkyl, $C_{2-30}$ alkenyl, $C_{2-30}$ alkynyl, $C_{3-30}$ cycloalkyl or $C_{4-30}$ aralkyl group optionally having one or more heteroatoms.

In certain embodiments, Y can be degradable under hydrolytic conditions. For example, Y can be selected from a carbonate linkage, an amide linkage, an ester linkage, or any combination thereof.

In some embodiments, $A^-$ can be chloride, bromide, iodide, sulfate, sulfonate or hydroxide ion.

In some instances, the surfactant of the present invention can be compound 1 or 2 or a mixture thereof:

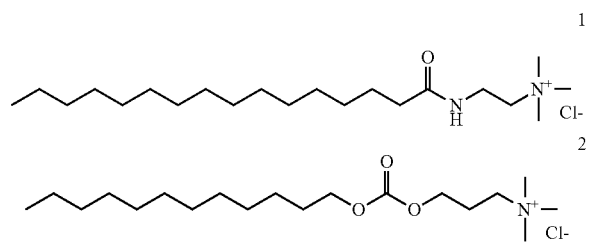

In another aspect of the present invention, an immunoassay kit is provided, comprising:
a) a chemiluminescent label having an acridinium dimethylphenyl ester, an acridinium sulfonamide, or a derivative or conjugate thereof;
b) an acidifying reagent comprising an acid, hydrogen peroxide and a degradable cationic surfactant having formula I:

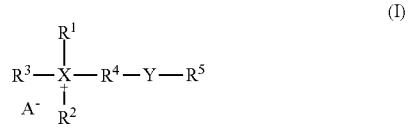

wherein $R^1$, $R^2$, $R^3$, $R^4$, $R^5$, Y and $A^-$ groups are defined as described herein; and
c) a basic reagent comprising alkaline hydroxide.

In some embodiments, the chemiluminescent label can be an acridinium dimethylphenyl ester, an acridinium sulfonamide, or a derivative or conjugate thereof.

In various embodiments, when in use, the surfactant of the present invention can provide a compressed emission time of the chemiluminescent label than a standard emission time without surfactants, wherein said compressed emission time is comparable to (e.g., about the same as, or about 20%, about 30% or about 50% shorter than) that of cetyltrimethylammonium chloride.

In certain embodiments, when in use, the surfactant of the present invention can exhibit an increased light emission of the chemiluminescent label compared to a standard light emission without surfactants, wherein said increased light emission is comparable to (e.g., at least about 70%, at least about 80% or at least about 90%) that of cetyltrimethylammonium chloride.

In some examples, the acid can be nitric acid. The alkaline hydroxide may be sodium hydroxide.

These and other aspect of the invention will be better understood by reference to the following detailed description, including the appended claims.

DETAILED DESCRIPTION

Figure 1:
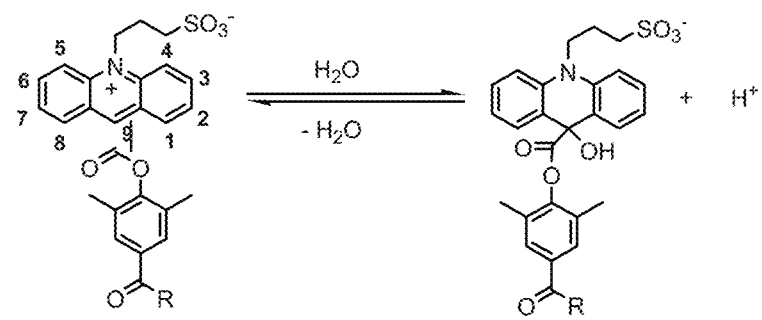
FIG. 1A: Acridinium-pseudobase equilibrium of an N-sulfopropyl acridinium dimethylphenyl ester.
FIG. 1B: Structures of chemiluminescent acridinium dimethylphenyl ester labels containing N-sulfopropyl groups in the acridinium ring that are used in automated immunoassays in Siemens Healthcare Diagnostics' ADVIA:Centaur® systems.
Figure 1:
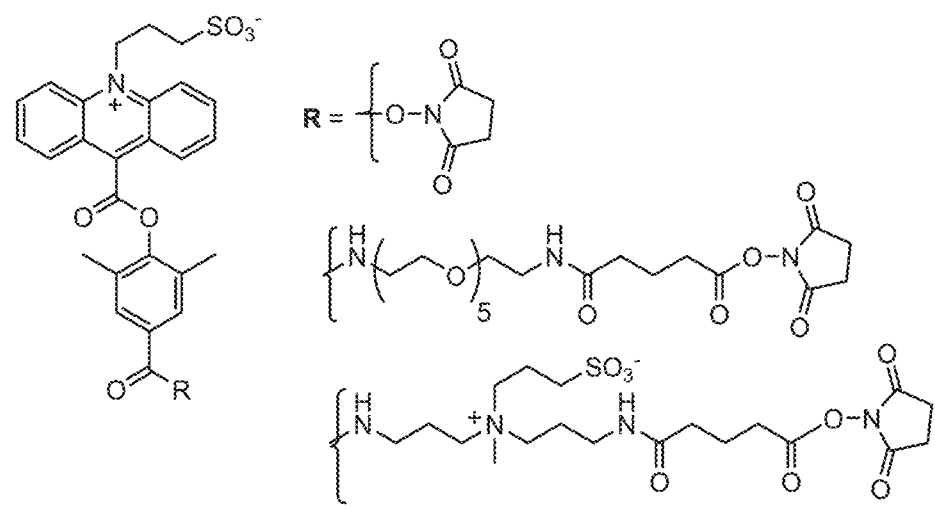

The present invention relates to methods of enhancing chemiluminescence from a chemiluminescent label comprising contacting a chemiluminescent label with an acid and hydrogen peroxide in the presence of a degradable cationic surfactant. Related kits containing such degradable cationic surfactant are also provided. The degradable cationic surfactant can compress light emission time of the chemiluminescent label to an extent that is comparable to or shorter than conventional surfactants. The degradable cationic surfactant can also increase chemiluminescence of the chemiluminescent label, providing increased light emission that is comparable to conventional surfactants.

To address the poor biodegradability of conventional cationic surfactants, especially under anaerobic conditions, the present invention introduces cleavable linkages between the quaternary head group and the alkyl chain of cationic surfactants. In the present invention, it is surprisingly found that cationic surfactants containing cleavable linkages (e.g., carbonate or amide) are at least as effective as CTAC in enhancing chemiluminescence from acridinium esters. The use of these environmentally friendly surfactants in light triggering reagents for widely used acridinium labels (e.g., esters or sulfonamides) is a green alternative to the conventional cationic surfactant CTAC.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein, the term "about" means within 20%, within 10% or within 5%.

The term "comparable" as used herein, means that a property of a first compound (e.g., a first surfactant) is about the same, or similar or equivalent to that of a second compound (e.g., a second surfactant). For example, when a property (e.g., compressed emission time or increased light emission) of a green surfactant of the present invention is referred to as being "comparable to that of cetyltrimethylammonium chloride," it is meant that such property is about the same as cetyltrimethylammonium chloride, the difference being within 20%, within 10% or within 5%. In some examples, the green surfactant of the present invention may exhibit better properties in light emission than cetyltrimethylammonium chloride.

In general, the term "surfactant" refers to compounds that lower the surface tension of a liquid, the interfacial tension between two liquids, or that between a liquid and a solid. Surfactants typically are chemicals that are amphipathic, which means that they contain both hydrophobic "head" and hydrophilic "tail" groups. Most commonly, surfactants are classified according to polar head group. A non-ionic surfactant has no charge groups in its head. The head of an ionic surfactant carries a net charge. If the charge is negative, the surfactant is more specifically called anionic; if the charge is positive, it is called cationic. If a surfactant contains a head with two oppositely charged groups, it is termed zwitterionic.

A "micelle" is an aggregate of surfactant molecules dispersed in a liquid colloid. A typical micelle in aqueous solution forms an aggregate with the hydrophilic head regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles may form when the concentration of surfactant is greater than the critical micelle concentration (CMC). Micelles can exist in different shapes, including spherical, cylindrical, and discoidal.

Green Surfactants

The main objective of the present invention is the elimination of the cationic surfactant CTAC and its replacement with more environmentally friendly, cationic surfactants in light triggering reagents for chemiluminescent acridinium labels.

In some embodiments, the structure of a degradable cationic surfactant for enhancing the chemiluminescence of acridinium ester labels can be represented by the following formula (I):

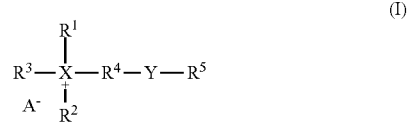

Wherein X is nitrogen or phosphorus; $R^1$, $R^2$ and $R^3$ are each independently selected from hydrogen and an alkyl, alkenyl, alkynyl, cycloalkyl or aralkyl group optionally having one or more heteroatoms; $R^4$ and $R^5$ are each independently selected from an alkyl, alkenyl, alkynyl, cycloalkyl or aralkyl group optionally having one or more heteroatoms; Y is a cleavable linkage; and $A^-$ is an anionic counterion.

In some embodiments, the structure of a degradable cationic surfactant for enhancing the chemiluminescence of acridinium ester labels can be represented by the following formula (II):

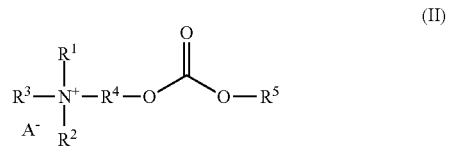

Wherein:
  $R^1$, $R^2$ and $R^3$ can be the same or different. For example, $R^1$, $R^2$ and $R^3$ can be each independently a $C_{1-10}$ alkyl, $C_{2-10}$ alkenyl, $C_{2-10}$ alkynyl, $C_{3-10}$ cycloalkyl or $C_{4-10}$ aralkyl group optionally having one or more heteroatoms (e.g., methyl, ethyl, propyl or butyl);
  $R^4$ can be a $C_{1-20}$ alkyl, $C_{2-20}$ alkenyl, $C_{2-20}$ alkynyl, $C_{3-20}$ cycloalkyl or $C_{4-20}$ aralkyl group optionally having one or more heteroatoms. For example, $R^4$ can be an alkyl chain comprising 2-4 carbons;
  $R^5$ can be a $C_{1-30}$ alkyl, $C_{2-30}$ alkenyl, $C_{2-30}$ alkynyl, $C_{3-30}$ cycloalkyl or $C_{4-30}$ aralkyl group optionally having one or more heteroatoms. For example, $R^5$ can be straight or branched alkyl chain (e.g., 10-16 carbons); and
  $A^-$ can be an anion selected from chloride, bromide, iodide, sulfate, sulfonate or hydroxide ions.

In another embodiment, the structure of a degradable cationic surfactant for enhancing the chemiluminescence of acridinium ester labels can be represented by the following formula (III):

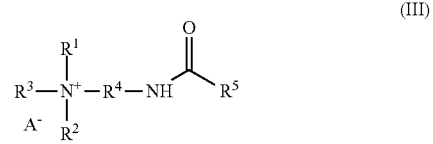

Wherein $R^1$, $R^2$, $R^3$, $R^4$, $R^5$ and $A^-$ can have the same definitions as above.

Other suitable surfactants with cleavable linkages as greener alternatives to conventional surfactants have been described elsewhere and are incorporated herein by reference (e.g., Tatsumi et al, *Journal of Surfactants and Detergents*, 2000, 3, 167-172; Tatsumi et al, *Journal of Surfactants and Detergents*, 2001, 4, 279-285; Banno et al, *Journal of Surfactants and Detergents*, 2009, 12, 249-259; Banno et al, *Journal of Surfactants and Detergents*, 2010, 13, 387-398; Banno et al, *Journal of Oleo Science*, 2011, 60, 117-126; Banno et al, *Journal of Oleo Science*, 2007, 56, 493-499; Stjerndahl and Holmberg, *J. Colloid and Interface Sci.*, 2005, 291, 570-576). Methods of making the above surfactants are known in the art.

Acridinium Compounds

The acridinium esters whose chemiluminescence can be enhanced by the degradable cationic surfactants can be represented by the following formula:

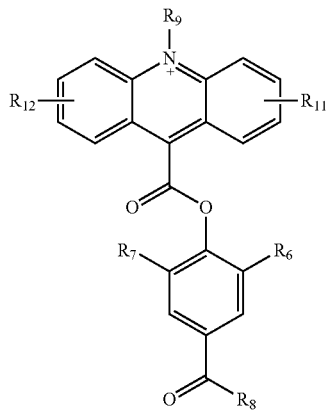

Wherein $R_6$, $R_7$, $R_8$ and $R_9$ can be alkyl, alkenyl, alkynyl or aralkyl groups containing 0-20 heteroatoms; $R_{10}$ and $R_{11}$ can be hydrogen, alkyl, alkenyl, alkynyl or aralkyl groups containing 0-20 heteroatoms.

Other suitable acridinium compounds (e.g., acridinium sulfonamides) include those described in U.S. Pat. Nos. 8,293,908; 8,119,422; 7,875,467; 7,785,904; 7,611,909; and 7,459,284; and U.S. Pub. Nos. 2012/0225497, 2010/0256380 and 2010/0099077; all of which are hereby incorporated herein by reference in their entirety.

Use of Green Surfactants

Compared to conventional cationic surfactants such as cetyltrimethylammonium chloride (CTAC), the use of degradable cationic surfactants is advantageous because they are rapidly degraded under both aerobic and anaerobic conditions and therefore pose a significantly lower risk when discharged into the environment. These cationic surfactants are also useful for enhancing the chemiluminescence of other labels such as acridinium sulfonamides whose light emission pathway is identical to that of acridinium esters.

Thus, one aspect of the present invention relates to a method of enhancing chemiluminescence from a chemiluminescent label comprising contacting a chemiluminescent label with an acid and hydrogen peroxide in the presence of a degradable cationic surfactant described herein. In certain embodiments, the method can further include compressing light emission time of the chemiluminescent label, thereby providing a compressed emission time than a standard emission time without surfactants. Such compressed emission time can be comparable to that of cetyltrimethylammonium chloride. For example, the compressed emission time may be shorter (e.g., about 20%, about 30% or about 50% shorter) than that of cetyltrimethylammonium chloride. In one embodiment, the surfactant of the present invention can be as effective as cetyltrimethylammonium chloride in enhancing total light yield of the chemiluminescent label.

In some embodiments, the method can further include enhancing chemiluminescence of said chemiluminescent label, thereby providing an increased light emission than a standard light emission without surfactants. Such increased light emission can be comparable to that of cetyltrimethylammonium chloride. For example, said increased light emission may be at least about 2.5 fold enhancement compared to the standard light emission without surfactants. In certain embodiments, such enhancement can be at least about 70%, at least about 80% or at least about 90% that of cetyltrimethylammonium chloride. In an embodiment, the surfactant of the present invention can be at least as effective as cetyltrimethylammonium chloride in compressing emission time of the chemiluminescent label.

In another aspect of the present invention, an immunoassay kit is provided, comprising:
 a) a chemiluminescent label having an acridinium dimethylphenyl ester, an acridinium sulfonamide, or a derivative or conjugate thereof;
 b) an acidifying reagent comprising an acid and a degradable cationic surfactant described herein; and
 c) an oxidizing reagent comprising alkaline hydrogen peroxide.

In various embodiments, when in use, the surfactant of the present invention can provide a compressed emission time of the chemiluminescent label than a standard emission time without surfactants. Such compressed emission time may be comparable to (e.g., about the same as, or about 20%, about 30% or about 50% shorter than) that of cetyltrimethylammonium chloride. In certain embodiments, when in use, the surfactant of the present invention can alternatively or additionally exhibit an increased light emission of the chemiluminescent label compared to a standard light emission without surfactants, such that the increased light emission may be comparable to (e.g., at least about 70%, at least about 80% or at least about 90%) that of cetyltrimethylammonium chloride.

In summary, it has been advantageously discovered that degradable cationic surfactants such as those containing cleavable amide and carbonate linkages are at least as effective as conventional cationic surfactants such as CTAC in enhancing the chemiluminescence of widely used acridinium ester labels. It was also surprisingly discovered that degradable cationic surfactants can be more effective in accelerating light emission than CTAC. The degradable surfactants show excellent stability in acidic solution and are environmentally friendly alternatives to CTAC. These surfactants are also useful in enhancing the luminescence of other labels such as acridinium sulfonamides. Because perturbations of chemical reactions rely on the ability of surfactants to increase the local concentrations of reactants and/or alter the polarity of the reaction medium, degradable surfactants can serve as benign alternatives to conventional surfactants for such applications.

EXAMPLES

Figure 3:
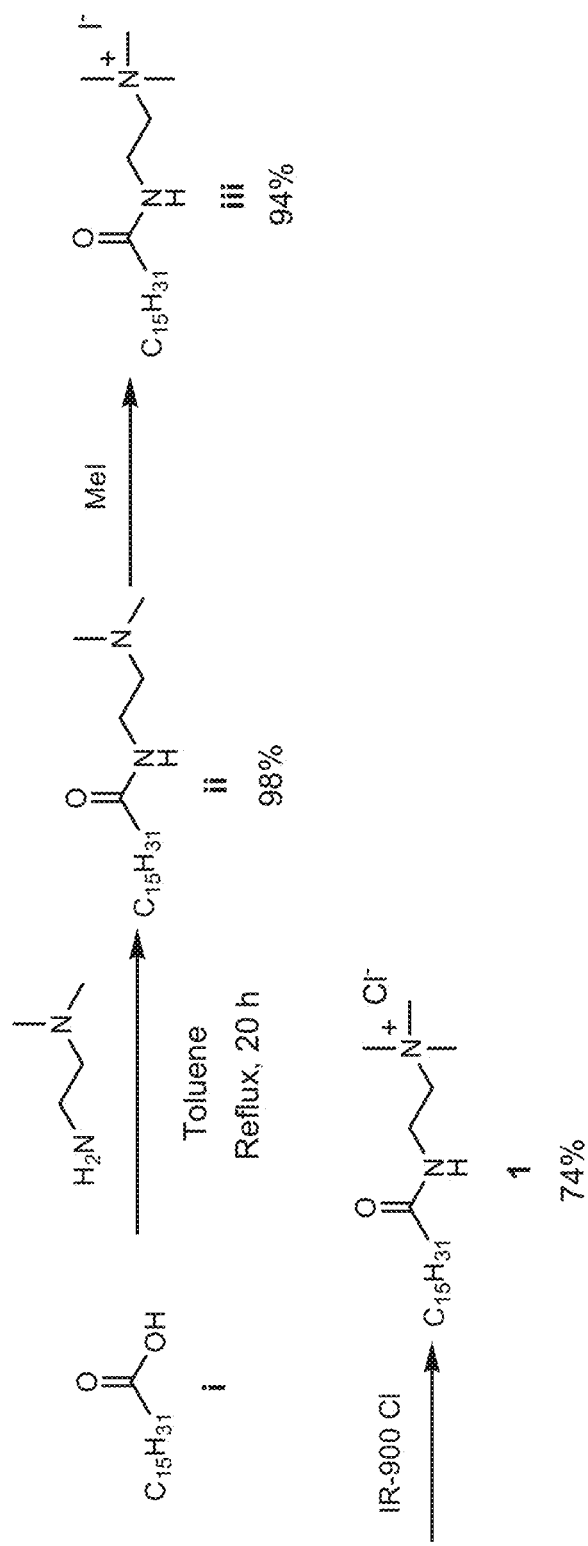
FIG. 3: Exemplary synthetic scheme for cationic surfactant 1 with cleavable amide linkage.

Example 1: Synthesis of Cationic Amide Surfactant 1 (FIG. 3)

Compound ii

Palmitic acid (i, 2.564 g, 10.00 mmoles), toluene (100 mL) and N,N-dimethylethylenediamine (1.147 mL, 10.50 mmoles) were combined and refluxed for 20 hours. The reaction mixture was concentrated to dryness which gave 3.21 g of a slightly yellow solid. The crude solid was re-crystallized from dry acetone (75 mL). The desired product ii (1.83 g) was obtained as white, needle-like crystals. $^1$H-NMR (500 MHz, CDCl$_3$), 0.87 (t, 3H, J=6.5), 1.20-1.35 (m, 24H), 1.55-1.70 (m, 2H), 2.17 (t, 2H, J=7.5), 2.30 (s, 6H), 2.49 (t, 2H, J=5.5), 3.36 (dt, 2H, J=5.5, 5.5), 6.25 (br s, 1H). MALDI-TOF MS m/z 327.4 (M+H$^+$); HRMS m/z 327.3376 (M+H$^+$) (327.3375 calculated).

Compound iii

Compound ii (1.41 g, 4.32 mmoles), acetone (50 mL) and iodomethane (0.309 mL, 4.97 mmoles) were refluxed at 80° C. under an argon atmosphere for 6 hours. The reaction mixture was cooled to room temperature and the precipitated white solid was collected by filtration. The filter cake was washed with dry acetone (10 mL×4) and dried over P$_2$O$_5$ under high vacuum. The desired product iii (1.904 g) was obtained as a white solid. $^1$H-NMR (500 MHz, CDCl$_3$) 0.88 (t, 3H, J=6.5), 1.21-1.38 (m, 22H), 1.57-1.70 (m, 4H), 2.29 (t, 2H, J=7.3), 3.42 (s, 9H), 3.78-3.89 (m, 4H), 7.96 (br s, 1H). MALDI-TOF MS m/z 282.36 (M-NMe$_3$$^+$); HRMS m/z 341.3528 (M$^+$) (341.3532 calculated).

Compound 1

Compound iii (1.50 g, 3.20 mmoles) was dissolved in absolute ethanol (400 mL) at room temperature and IR-900 chloride resin (76.2 g, 3.20 mmoles) was added and stirred at room temperature for 1 hour. Then, the mixture was passed through an IR-900 chloride resin column (80 g pre-washed with absolute ethanol). The column was eluted with absolute ethanol (600 mL). The eluent was concentrated under reduced pressure which gave 1.51 g of a slightly brown solid. This material was re-crystallized from anhydrous acetone/ethanol. The desired product, surfactant 1 (0.895 g), was obtained as a white solid. $^1$H-NMR (500 MHz, CDCl$_3$) 0.86 (t, 3H, J=6.3), 1.17-1.38 (m, 22H), 1.55-1.68 (m, 4H), 2.27 (t, 2H, J=7.3), 3.43 (s, 9H), 3.70-3.85 (m, 4H), 8.72 (br s, 1H). MALDI-TOF MS m/z 282.36 (M-NMe$_3$$^+$); HRMS m/z 341.3529 (M$^+$) (341.3532 calculated).

Figure 4:
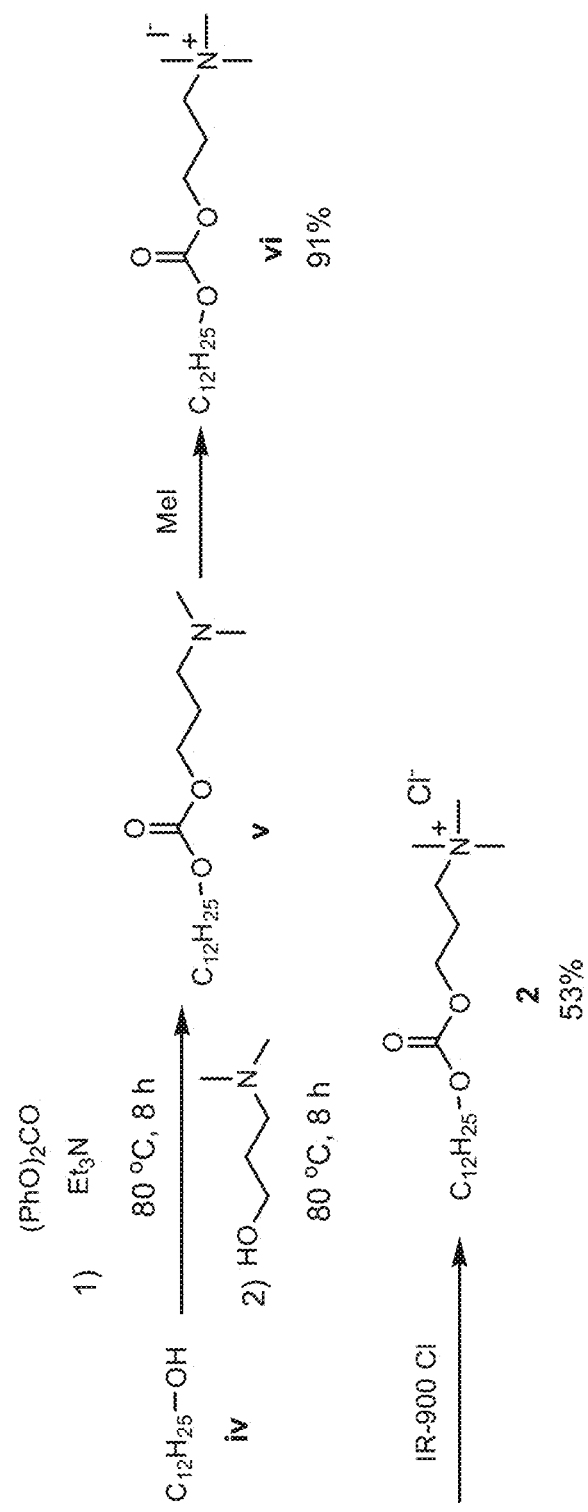
FIG. 4: Exemplary synthetic scheme for cationic surfactant 2 with cleavable carbonate linkage.

Example 2: Synthesis of Cationic Carbonate Surfactant 2 (FIG. 4)

Compound v

A mixture of dodecanol (iv, 2.236 mL, 10.00 mmoles), triethylamine (1.394 mL, 10.00 mmoles) and diphenyl carbonate (2.142 g, 10.00 mmoles) was heated to 80° C. for 16 hours. Then, 3-dimethylamino-1-propanol (2.366 mL, 20.00 mmoles) was added and heated to 80° C. for an additional 16 hours. The reaction mixture was then concentrated under reduced pressure to give 3.92 g of a dark yellow oil. It was purified by silica gel column chromatography using methanol/ethyl acetate (1:9) as eluent. The desired product v (2.63 g) was obtained as a yellow oil. $^1$H-NMR (500 MHz, CDCl$_3$) 0.88 (t, 3H, J=6.5), 1.20-1.42 (m, 18H), 1.61-1.71 (m, 2H), 1.87-1.98 (m, 2H), 2.33 (s, 6H), 2.49 (br t, 2H, J=7.0), 4.12 (t, 2H, J=6.5), 4.19 (t, 2H, J=6.3). MALDI-TOF MS m/z 316.3 (M+H$^+$); HRMS m/z 316.2855 (M+H$^+$) (316.2852 calculated).

Compound vi

Compound v (1.500 g, 4.75 mmoles), acetone (50 mL) and iodomethane (0.340 mL, 5.47 mmoles) were combined and refluxed for 6 hours. After cooling to room temperature, the desired product precipitated out as a white solid. It was collected by filtration and washed with ethyl acetate (10 mL×4). The solid was dried over P$_2$O$_5$ under high vacuum. The desired product vi (1.988 g) was obtained as a white solid. $^1$H-NMR (500 MHz, CDCl$_3$) 0.87 (t, 3H, J=7.0), 1.60-1.72 (m, 18H), 2.05-2.34 (m, 2H), 3.49 (s, 9H), 3.76 (t, 2H, J=7.3), 4.12 (t, 2H, J=6.5), 4.29 (m, 2H). MALDI-TOF MS m/z 316.3 (M+H$^+$); HRMS m/z 316.2855 (M+H$^+$) (316.2852 calculated).

Compound 2

Compound vi (1.50 g, 3.28 mmoles) was dissolved in absolute ethanol (200 mL) at room temperature and IR-900 chloride resin (78 g, 328 mmoles) was added and stirred at room temperature for 1 hour. Then, the mixture was passed through an IR-900 chloride resin column (80 g pre-washed with absolute ethanol). The column was eluted with absolute ethanol (400 mL). The eluent was concentrated under reduced pressure which gave 1.5 g of a white solid. The crude product was re-crystallized from anhydrous acetone. The desired product 2 (0.637 g) was obtained as a white solid. $^1$H-NMR (500 MHz, CDCl$_3$) 0.86 (t, 3H, J=6.5) 1.60-1.70 (m, 18H), 2.18-2.30 (m, 2H), 3.49 (s, 9H), 3.72 (t, 2H, J=7.8), 4.11 (t, 2H, J=6.8), 4.25 (m, 2H). HRMS m/z 330.3013 (M$^+$) (330.3008 calculated).

Example 3: Chemiluminescence Measurements

Figure 2:
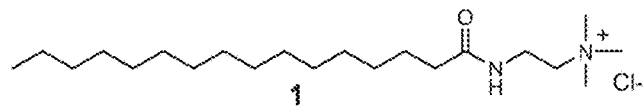
FIG. 2A: Structures of exemplary cationic surfactants (1 and 2) containing cleavable linkages (CMC=critical micelle concentration).
FIG. 2B: Structures of exemplary acridinium esters (3a, 3b and 3c) used to make anti-TSH antibody conjugates in the current study (TSH=thyroid stimulating hormone).
Figure 2:
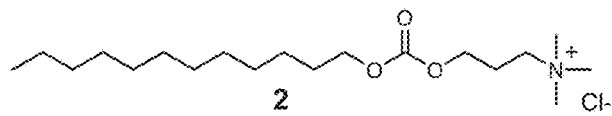
Figure 2:
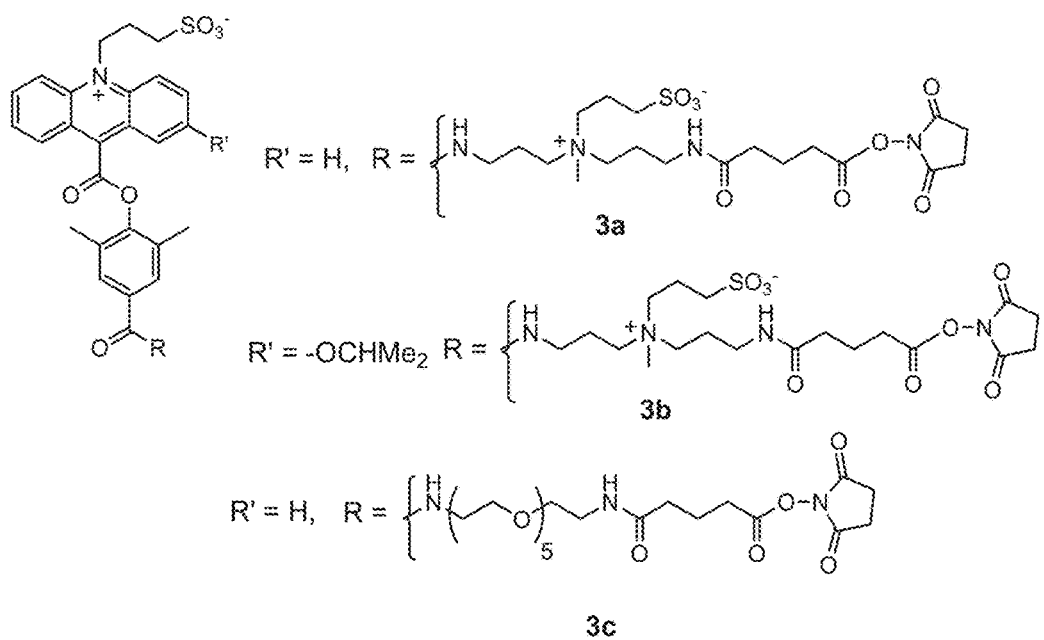

To study the impact of degradable cationic surfactants on acridinium ester chemiluminescence, two exemplary cationic surfactants containing cleavable linkages (FIG. 2A) were selected. The critical micelle concentrations (CMCs) of the two surfactants are shown in FIG. 2A. The synthetic schemes for the two surfactants are illustrated in FIGS. 3-4 and described in Examples 1 and 2 above. Both surfactants were dissolved in Reagent 1 (0.1 M nitric acid containing 0.5% hydrogen peroxide) at five times their reported CMCs in water. CTAC dissolved in Reagent 2 (0.25 M NaOH) was used as the control surfactant. The two carbonate and amide cationic surfactants (FIG. 2A) were dissolved in Reagent 1 to preserve stability, especially during long term storage (Stjerndahl and Holmberg, *J. Colloid and Interface Sci.*, 2005, 291, 570-576). Three acridinium esters (FIG. 2B, compounds 3a, 3b and 3c) were used to make protein conjugates of an anti-TSH antibody (TSH=thyroid stimulating hormone) as described in the literature (Natrajan et al, *Org. Biomol. Chem.*, 2011, 9, 5092-5103; Natrajan et al, *Org. Biomol. Chem.*, 2012, 10, 3432-3447). The conjugates contained approximately 5 labels. The conjugates were stored at 4° C. in buffer and chemiluminescence from each conjugate was measured in the absence of surfactant and in the presence of CTAC as well as cationic surfactants 1 and 2 (Tables 1-3, FIGS. 5-7). The ability of each surfactant to (a) increase total light output and (b) accelerate emission kinetics was evaluated over a period of 80 days.

Chemiluminescence of anti-TSH antibody conjugates of acridinium esters 3a, 3b and 3c (FIG. 2B) was measured on an Autolumat LB953 Plus luminometer from Berthold Technologies. The conjugates, ~2 mg/mL containing approximately five labels, were serially diluted 10$^5$-fold for chemiluminescence measurements in an aqueous buffer of 10 mM disodium hydrogen phosphate, 0.15 M NaCl and 8 mM sodium azide and 0.015 mM bovine serum albumin (BSA), pH 8.0. A 0.010 mL volume of each diluted acridinium ester sample was dispensed into the bottom of a cuvette. Cuvettes were placed into the primed LB953 and the chemiluminescence reaction was initiated with the sequential addition of 0.3 mL of Reagent 1, a solution of 0.5% hydrogen peroxide in 0.1 M nitric acid followed by the addition of 0.3 mL of Reagent 2, a solution of 0.25 M sodium hydroxide. For measurements in the presence of CTAC, the surfactant (7 mM) was included in Reagent 2. For measurements in the presence of the cationic amide surfactant 1 or the cationic carbonate surfactant 2, each surfactant was dissolved in Reagent 1 at 3.2 mM (surfactant 1) and 2.15 mM (surfactant 2). Each chemiluminescence flash curve was measured in 240 intervals of 0.5 second (120 seconds total time). Each chemiluminescence reaction was carried out a minimum of three times, averaged and converted to a percentage of the chemiluminescence accumulated up to each time interval. The output from the luminometer instrument was expressed as R.L.U.s (Relative Light Units).

The results in Tables 1-3 illustrate that both the cationic surfactants 1 and 2 containing cleavable amide and carbonate linkages respectively, are at least as effective as CTAC in not only increasing total light yield from the acridinium ester conjugates but also in compressing emission times. For example, for all three acridinium ester conjugates, in comparison to the no surfactant control which was assigned a relative light yield of one, total light yield was increased approximately 2.5-4-fold for 3a, 3-5-fold for 3b and 3-4.5-fold for 3c (Tables 1a, 2a and 3a) for CTAC as well as surfactants 1 and 2. Specifically, Table 1a shows that surfactant 2 is as effective as CTAC within at least the first 10 days in enhancing chemiluminescence (i.e., the fold of increased light emission by surfactant 2 is the same as CTAC). Even at day 80, the fold of increased light emission using surfactant 2 remains to be about 80% (2.8/3.5) of CTAC. Similarly, the fold of increased light emission using Surfactant 1 is about 89% (3.1/3.5) on day 1, and 74% (2.6/3.5) on day 80 compared to CTAC. Thus, both surfactants 1 and 2 are comparable to CTAC in enhancing chemiluminescence. In addition, the two cationic surfactants 1 and 2 proved to be quite stable in Reagent 1 (0.5% peroxide in 0.1 M nitric acid) as evidenced by little loss in their ability to enhance chemiluminescence from the acridinium ester antibody conjugates even after 80 days at room temperature.

Figure 5:
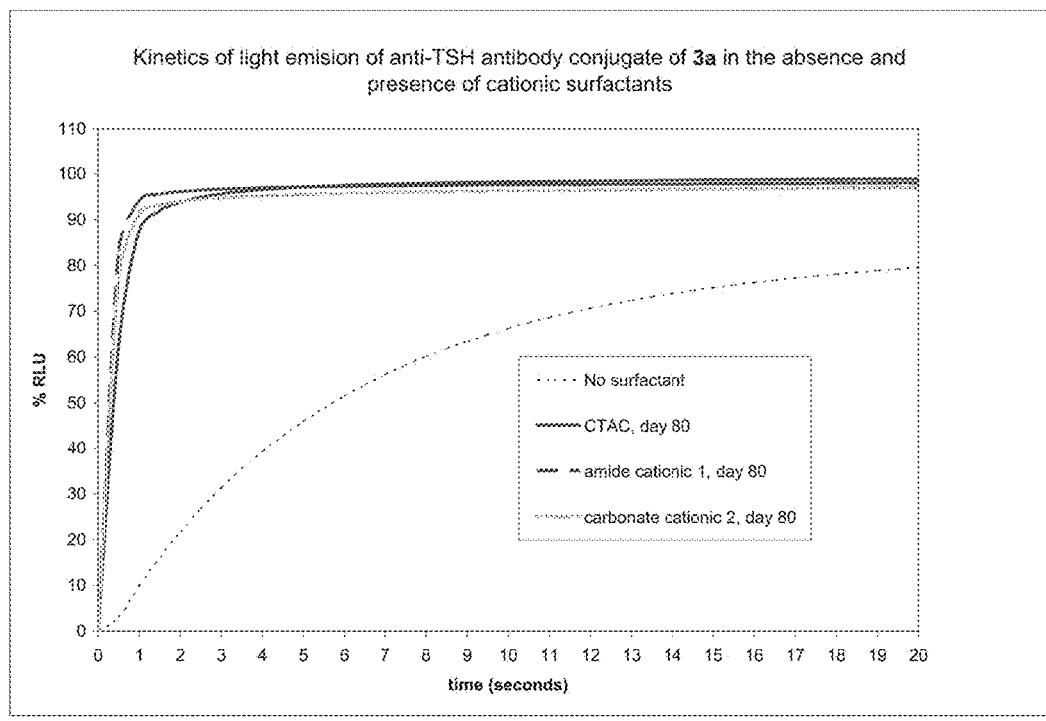
FIG. 5: Chemiluminescence emission profiles of anti-TSH antibody conjugate of acridinium ester 3a in the absence and presence of cationic surfactants. (RLU=Relative Light Unit).
Figure 6:
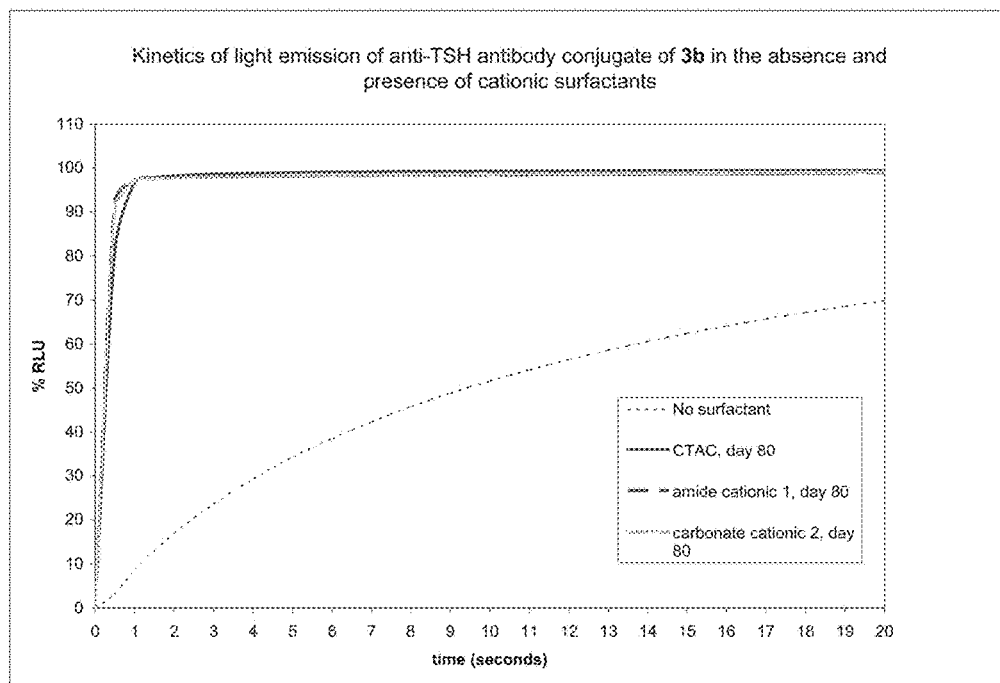
FIG. 6: Chemiluminescence emission profiles of anti-TSH antibody conjugate of acridinium ester 3b in the absence and presence of cationic surfactants.
Figure 7:
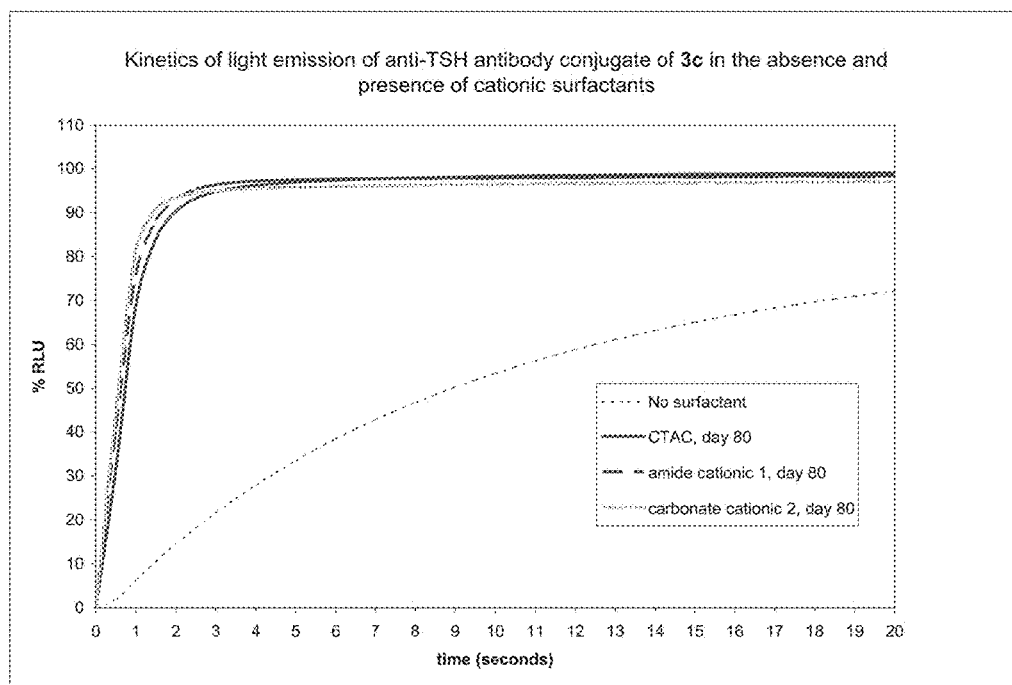
FIG. 7: Chemiluminescence emission profiles of anti-TSH antibody conjugate of acridinium ester 3c in the absence and presence of cationic surfactants.

Furthermore, both surfactants 1 and 2 were very effective in accelerating light emission from the acridinium ester antibody conjugates (Tables 1b, 2b and 3b, FIGS. 5-7). In the absence of surfactant, times for emission of >90% light from the conjugates of 3a, 3b and 3c were observed to be 57.5 seconds, 49.5 seconds and 62.5 seconds respectively. In the presence of CTAC or the two cationic surfactants 1 and 2, emission times were compressed to <3 seconds for the conjugates of all three acridinium ester labels. Surprisingly, surfactants 1 and 2 are more effective than CTAC in accelerating light emission. For example, as shown in Table 1b, both surfactants 1 and 2 accelerated emission kinetics of acridinium ester 3a from 57.5 seconds to 1.0 second, while CTAC was 1.5 seconds. The ability of the two cationic surfactants 1 and 2 to accelerate light emission did not diminish even after 80 days of storage at room temperature as also illustrated in the chemiluminescence emission profiles of the conjugates (FIGS. 5-7).

EQUIVALENTS

The present invention provides among other things green surfactants and their use in enhancing chemiluminescence. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent was specifically and individually indicated to be incorporated by reference.

TABLE 1a

Observed enhancement (fold) of chemiluminescence of anti-TSH antibody conjugate of acridinium ester 3a (no surfactant control was assigned a value of 1).

| Day | CTAC | Amide cationic 1 | Carbonate cationic 2 |
| --- | --- | --- | --- |
| 1 | 3.5 | 3.1 | 3.5 |
| 10 | 3.6 | 3.1 | 3.6 |
| 20 | 4.0 | 3.4 | 3.7 |
| 40 | 3.4 | 2.6 | 3.2 |
| 80 | 3.5 | 2.6 | 2.8 |

TABLE 1b

Observed acceleration of emission kinetics (time to >90% emission in seconds) of anti-TSH antibody conjugate of acridinium ester 3a (in the absence of surfactant time to >90% emission was 57.5 seconds).

| Day | CTAC | Amide cationic 1 | Carbonate cationic 2 |
| --- | --- | --- | --- |
| 1 | 1.5 | 1.0 | 1.0 |
| 10 | 1.5 | 1.0 | 1.0 |
| 20 | 1.5 | 1.0 | 1.0 |
| 40 | 1.5 | 1.0 | 1.0 |
| 80 | 1.5 | 1.0 | 1.0 |

TABLE 2a

Observed enhancement (fold) of chemiluminescence of anti-TSH antibody conjugate of acridinium ester 3b (no surfactant control was assigned a value of 1).

| Day | CTAC | Amide cationic 1 | Carbonate cationic 2 |
| --- | --- | --- | --- |
| 1 | 5.3 | 4.5 | 5.0 |
| 10 | 5.2 | 4.4 | 5.2 |
| 20 | 5.5 | 4.7 | 5.2 |
| 40 | 4.2 | 3.4 | 3.9 |
| 80 | 4.6 | 3.4 | 4.1 |

TABLE 2b

Observed acceleration of emission kinetics (time to >90% emission in seconds) of anti-TSH antibody conjugate of acridinium ester 3b (in the absence of surfactant time to >90% emission was 49.5 seconds).

| Day | CTAC | Amide cationic 1 | Carbonate cationic 2 |
| --- | --- | --- | --- |
| 1 | 1.0 | 1.0 | 0.5 |
| 10 | 1.0 | 0.5 | 0.5 |
| 20 | 1.0 | 0.5 | 0.5 |
| 40 | 1.0 | 0.5 | 0.5 |
| 80 | 1.0 | 0.5 | 0.5 |

TABLE 3a

Observed enhancement (fold) of chemiluminescence of
anti-TSH antibody conjugate of acridinium ester 3c
(no surfactant control was assigned a value of 1).

| Day | CTAC | Amide cationic 1 | Carbonate cationic 2 |
|---|---|---|---|
| 1 | 4.1 | 3.8 | 4.2 |
| 10 | 4.3 | 3.8 | 4.2 |
| 20 | 4.6 | 4.1 | 4.4 |
| 40 | 3.9 | 3.2 | 3.7 |
| 80 | 4.0 | 3.0 | 3.5 |

TABLE 3b

Observed acceleration of emission kinetics (time to >90%
emission in seconds) of anti-TSH antibody conjugate of acridinium
ester 3c (in the absence of surfactanttime
to >90% emission was 62.5 seconds).

| Day | CTAC | Amide cationic 1 | Carbonate cationic 2 |
|---|---|---|---|
| 1 | 2.0 | 2.0 | 1.0 |
| 10 | 2.0 | 2.0 | 1.0 |
| 20 | 2.5 | 2.0 | 1.5 |
| 40 | 2.5 | 2.0 | 1.5 |
| 80 | 2.5 | 2.0 | 1.5 |

The invention claimed is:

1. A method of enhancing chemiluminescence from a chemiluminescent label, comprising contacting a chemiluminescent label with an acid and hydrogen peroxide in the presence of a degradable cationic surfactant having formula I:

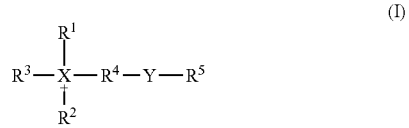

wherein:
X is nitrogen or phosphorus;
$R^1$, $R^2$ and $R^3$ are each independently selected from hydrogen and an alkyl, alkenyl, alkynyl, cycloalkyl or aralkyl group optionally having one or more heteroatoms;
$R^4$ and $R^5$ are each independently selected from an alkyl, alkenyl, alkynyl, cycloalkyl or aralkyl group optionally having one or more heteroatoms;
Y is a cleavable linkage selected from the group consisting of a carbonate linkage, an amide linkage, an ester linkage and any combination thereof; and
$A^-$ is an anionic counterion to $X^+$,
wherein said chemiluminescent label is an acridinium dimethylphenyl ester, an acridinium sulfonamide, or a derivative or conjugate thereof.

2. The method of claim 1, wherein said surfactant provides a compressed emission time of said chemiluminescent label shorter than that of cetyltrimethylammonium chloride.

3. The method of claim 2, wherein said compressed emission time is about 20% shorter than that of cetyltrimethylammonium chloride.

4. The method of claim 2, wherein said compressed emission time is about 30% shorter than that of cetyltrimethylammonium chloride.

5. The method of claim 2, wherein said compressed emission time is about 50% shorter than that of cetyltrimethylammonium chloride.

6. The method of claim 1, wherein said surfactant is as effective as cetyltrimethylammonium chloride in enhancing total light yield of the chemiluminescent label.

7. The method of claim 1, wherein the chemiluminescence of said chemiluminescent label is increased, thereby providing an increased light emission relative to a standard light emission without surfactants.

8. The method of claim 7, wherein said increased light emission is at least about 2.5 fold enhancement compared to the standard light emission without surfactants.

9. The method of claim 7, wherein said enhancement is at least about 70% that of cetyltrimethylammonium chloride.

10. The method of claim 7, wherein said enhancement is at least about 80% that of cetyltrimethylammonium chloride.

11. The method of claim 7, wherein said enhancement is at least about 90% that of cetyltrimethylammonium chloride.

12. The method of claim 7, wherein said surfactant is at least as effective as cetyltrimethylammonium chloride in compressing emission time of the chemiluminescent label.

13. The method of claim 1, wherein $R^1$, $R^2$ and $R^3$ are each independently a $C_{1-10}$ alkyl, $C_{2-10}$ alkenyl, $C_{2-10}$ alkynyl, $C_{3-10}$ cycloalkyl or $C_{4-10}$ aralkyl group optionally having one or more heteroatoms.

14. The method of claim 1, wherein $R^4$ is a $C_{1-20}$ alkyl, $C_{2-20}$ alkenyl, $C_{2-20}$ alkynyl, $C_{3-20}$ cycloalkyl or $C_{4-20}$ aralkyl group optionally having one or more heteroatoms.

15. The method of claim 1, wherein $R^5$ is a $C_{1-30}$ alkyl, $C_{2-30}$ alkenyl, $C_{2-30}$ alkynyl, $C_{3-30}$ cycloalkyl or $C_{4-30}$ aralkyl group optionally having one or more heteroatoms.

16. The method of claim 1, wherein Y is degradable under hydrolytic conditions.

17. The method of claim 1, wherein $A^-$ is chloride, bromide, iodide, sulfate, sulfonate or hydroxide ion.

18. The method of claim 1, wherein said surfactant is compound 1 or 2 or a mixture thereof:

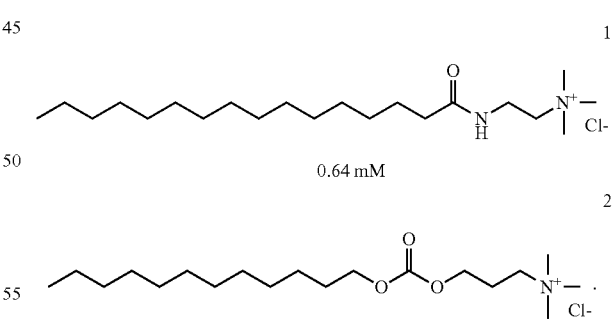

19. The method according to claim 1, wherein $R^1$-$R^3$ are each independently alkyl optionally having one or more heteroatoms.

20. The method according to claim 1 wherein $R^4$ and $R^5$ are independently selected from alkyl, cycloalkyl, or aralkyl optionally having one or more heteroatoms.

* * * * *